United States Patent [19]

Lueders et al.

[11] 4,439,179

[45] Mar. 27, 1984

[54] DUAL TUBING CLAMP

[75] Inventors: Arthur Lueders, Mundelein; Marc Bellotti, Winnetka, both of Ill.

[73] Assignee: Baxter Travenol Laboratories, Inc., Deerfield, Ill.

[21] Appl. No.: 349,274

[22] Filed: Feb. 16, 1982

[51] Int. Cl.³ .................... A61M 1/03; F16L 55/14
[52] U.S. Cl. ............................... 604/34; 604/250; 604/29; 251/7
[58] Field of Search ............... 604/29, 30, 33, 34, 604/32, 249, 250, 251; 251/7; 137/595

[56] References Cited

U.S. PATENT DOCUMENTS 3,316,935 3/1967 Kaiser et al. ................ 604/250
3,985,134 10/1976 Ussot et al. ................. 604/34 X
4,061,142 12/1977 Tuttle ........................... 604/34

Primary Examiner—Stephen C. Pellegrino
Attorney, Agent, or Firm—Paul C. Flattery; Garrettson Ellis

[57] ABSTRACT

There is disclosed herein a dual flow control clamp for use in continuous ambulatory peritoneal dialysis wherein a patient is connected to the source of dialysis solution through a branched flow path. One branch controls flow to the patient and the other branch controls flow from the patient. The clamp provides for selectively controlling flow in one or both flow paths, while never permitting flow simultaneously in both flow paths.

24 Claims, 8 Drawing Figures

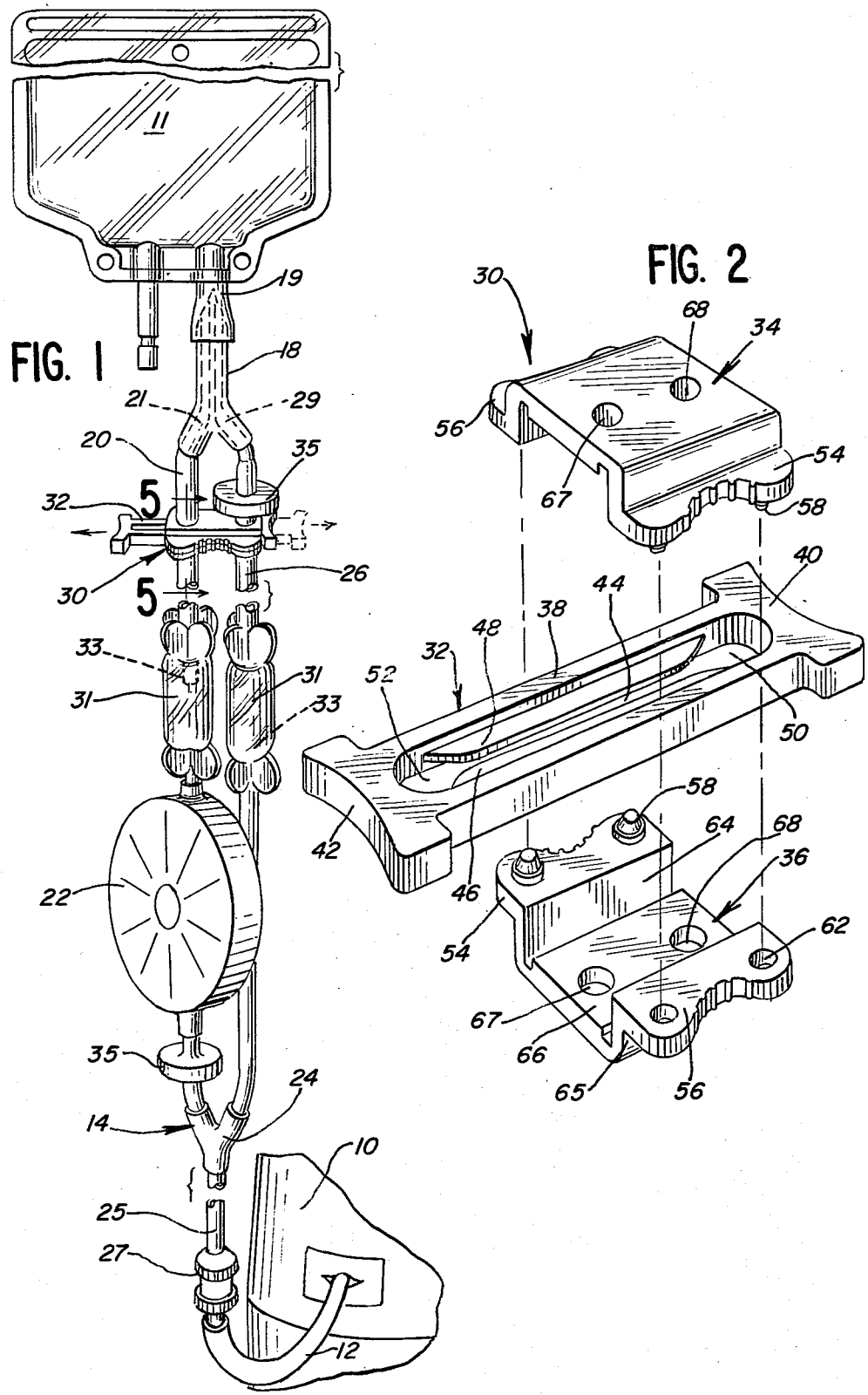

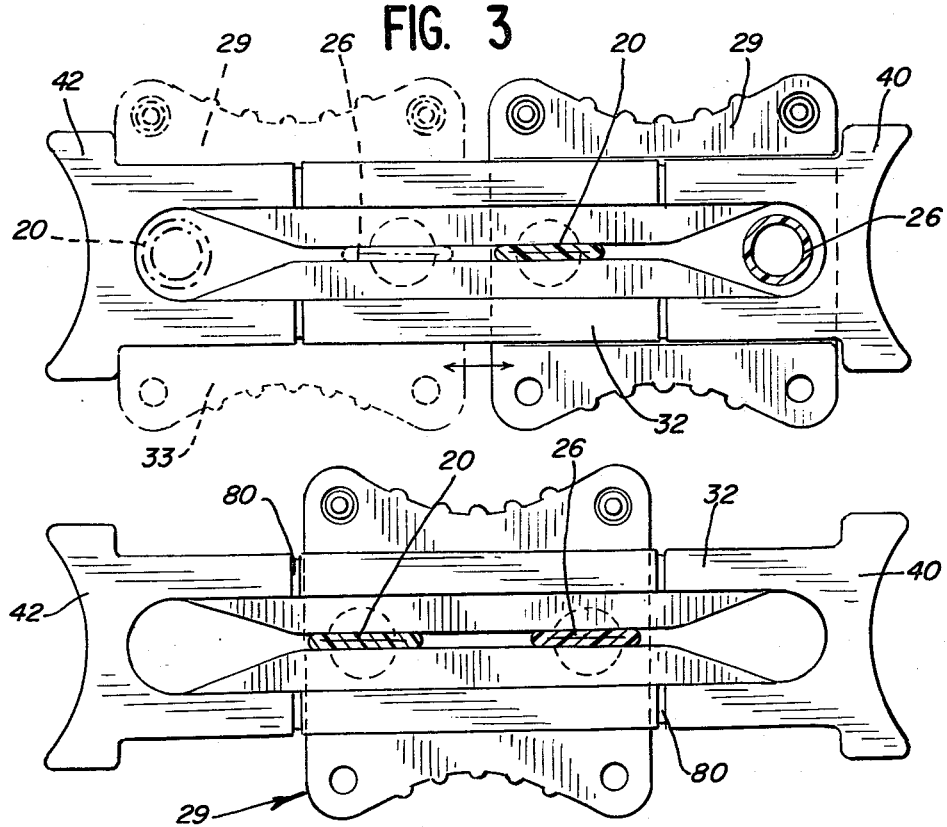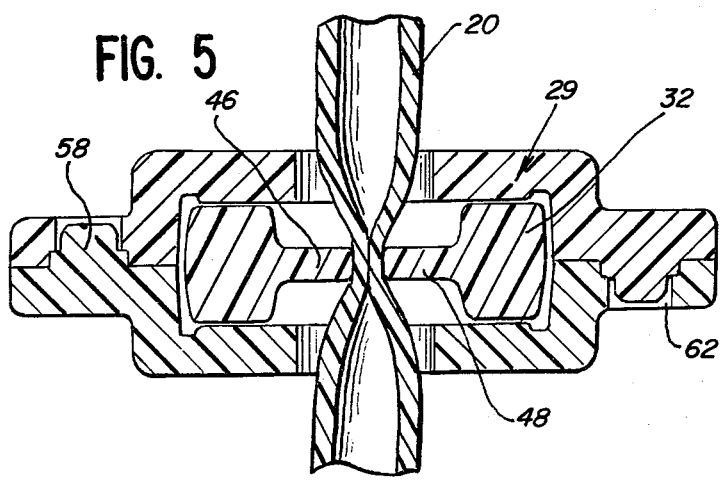

DUAL TUBING CLAMP

BACKGROUND OF THE INVENTION

This invention relates to a peritoneal dialysis set, and more particularly, to a flow control slide clamp for such set.

Continuous ambulatory peritoneal dialysis (CAPD) is a relatively new and fast developing form of peritoneal dialysis for use in maintenance of patients with end stage renal disease. CAPD has advantages over and is replacing certain other forms of dialysis such as hemodialysis. Other forms of peritoneal dialysis are also growing in popularity, for example, continuous cycling peritoneal dialysis.

In CAPD a patient is connected via a catheter and tubing set to a source, usually a bag, of fresh dialysis solution. The patient's peritoneal cavity is filled with solution by draining the solution from the bag into the peritoneal cavity. After filling, the tubing leading to the patient is closed, and dialysis begins. After the dialysis treatment is completed, in about four to six hours, the spent solution is drained from the peritoneal cavity back to the bag, and a bag with fresh solution replaces the bag of spent solution.

Until recently the flow path has been a single tube which conducted solution both to and from the patient. However, in French Patent No. 2,455,462 the flow path between the bag and the patient's catheter is split into two rejoining branches. One branch is intended for flow of fresh solution to the patient, and the other for flow of spent or used solution from the patient. A filter is placed in the branch for flow to the patient.

Since there are two branches communicating with the patient, one of which includes a filter, it is important to maintain control and flow in the proper directions. For example, it is important to prevent any flow of spent dialysis solution through the filter, since the filter can be easily clogged by spent dialysis solution which has picked up clogging agents while residing in the peritoneal cavity. Thus, flow in the two branches is best maintained in the proper direction.

Furthermore, during exchange, it is important to be able to control the flow in one or the other branches and to cease flow in both branches, while also preventing simultaneous flow in both branches, so that spent dialysis solution will not siphon into the inflow branch, for example.

Furthermore, the apparatus for controlling flow should be compact, of simple design and readily usable by a patient.

SUMMARY OF THE INVENTION

There is provided by this invention a slide clamp for controlling the flow of dialysis solution between a dialysis solution bag and a patient where the flow paths are branched to form one tubular branch line leading to the patient and another tubular branch line leading from the patient. The flow in these branches is desirably maintained in proper directions. The clamp provides for selectively preventing flow in one or both branches, while never permitting simultaneous flow in both branches.

The clamp includes an elongated, slotted slide member having internally-extending ribs or shoulders that define open branch-receiving openings at each end of the slot, and a narrow branch-receiving and closing slit intermediate the tube openings.

The clamp also includes a slide housing which is constructed to overlie the slide member. The housing includes a pair of aligned aperture means through which the tubular branches pass. The housing aperture means are spaced apart a distance less than the distance between the open branch-receiving openings of the slide member so as to prevent simultaneous alignment between both housing aperture means and both open branch-receiving openings.

The clamp of this invention also includes an enlarged head section at each end of the slide member, with each head being adapted to engage the slide housing and thus limit the movement of the slide member.

The structure of the slide member is such that in all sliding positions at least one of the tubular branches occupies the narrow branch-receiving and closing slit between the ribs, so that in all positions at least one of the tubular branches is closed. When the slide clamp is placed in a central position relative to the slide housing, both of the tubular branches reside in the narrow branch receiving and closing slit, and are thus closed. When the slide member is positioned in one of its extreme sliding positions, where one of the enlarged head sections are adjacent to or engage the slide housing, one of the branch tubes occupies an open branch-receiving opening to permit flow therethrough.

The above clamp may be carried on a tubular set for conveying peritoneal dialysis solution between a patient and a solution container with the clamp being retained in a fixed position adjacent the end of the set which connects with the solution container. The set has the tubular branches as described above extending through the clamp in the relationship so described for flow control therethrough.

The tubular branches may each include a length of tubular, cross-linked elastomer such as silicone rubber as at least a part thereof, with the length of tubular, elastomer extending within the slide housing, to be acted upon by the slide member. The remainder of the tubular set may comprise tubing of a different, flexible thermoplastic formulation, for example a polyvinyl chloride formulation, connected to the cross-linked elastomer. The tubular, cross-linked elastomer is thus acted on by the clamp of this invention and exhibits little or no cold flow to interfere with the clamping operation, as is a problem with thermoplastic formulations such as polyvinyl chloride.

Alternatively, the clamp may be carried in fixed position between a pair of retaining sleeve members attached to the tubular set.

Also, the set of this invention may have a double lumen spike at the end that connects with the solution container. The tubular branches each connect with a separate lumen of the spike to define separate flow paths through the spike and branches. This substantially eliminates the prior art problem that, as spent peritoneal dialysis solution drains through a connection spike back into its container as is known procedure for peritoneal dialysis, a small amount of the spent solution remains in the single lumen of a spike at the end of the drainage phase. Thereafter, fresh dialysis solution flows through the spike and the filter in the inflow phase, where the fresh dialysis solution passes back to the patient, carrying the small amount of spent peritoneal dialysis solution retained within the spike lumen with it.

It has been found that even this small amount of spent peritoneal dialysis solution, when run back through the filter day after day in the normal routine of peritoneal dialysis, can cause the filter to degrade by clogging before it may become otherwise desirable to replace the peritoneal dialysis set. Accordingly, the use of a double lumen spike substantially eliminates this problem, since the solution inflow takes place through a different lumen of the spike than does the outflow of spent peritoneal dialysis solution.

BRIEF DESCRIPTION OF THE DRAWINGS

FIG. 1 is a perspective view showing a set having the tubular branches and flow control clamp described above for connecting a patient to a bag of dialysis solution;

FIG. 2 is an exploded perspective view showing the clamp of FIG. 1, including a slide housing in two halves and a slide member;

FIG. 3 is a plan view showing two positions of the slide member relative to the slide housing, the slide housing being shown in two different positions relative to the slide member, with one branch open and one branch closed in each position;

FIG. 4 is a plan view showing the slide member in a third position to close both branches;

FIG. 5 is a longitudinal sectional view taken along line 5—5 of FIG. 1, showing a portion of a branch being grasped by the clamp.

DESCRIPTION OF THE PREFERRED EMBODIMENT

Figure 6:
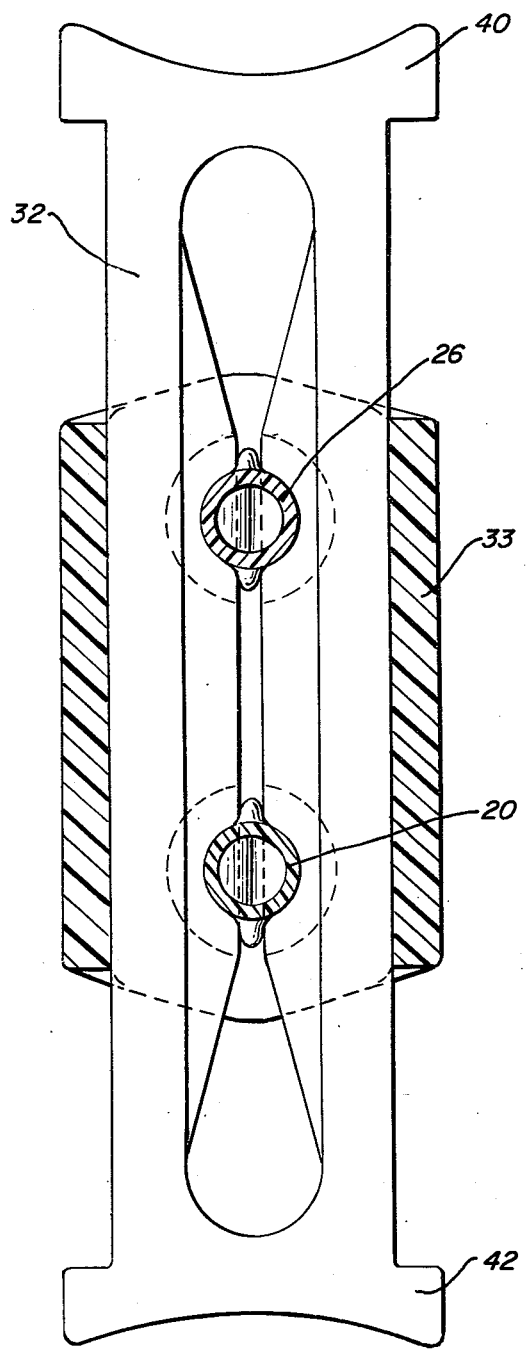
FIG. 6 is a transverse sectional view showing the slide member in position closing both branches.

Referring now to FIG. 1, the peritoneal cavity of patient 10 is shown connected to a dialysis solution bag 11 via catheter 12 and a branched tubing set 14.

The dialysis solution bag 11 is coupled to tube set 14 by double lumen piercing spike 18 which may pass into a conventional diaphram port 19 of bag 11.

The tubing set 14 is made of flexible plastic, and branches into tubular branch 20, which extends from first lumen 21 of spike 18 through filter 22 to Y-connection 24, where it joins set tube 25 which can communicate with catheter 12 through a conventional connector 27.

Branch 20 constitutes the "to" or "fill" line for fresh dialysis solution flow from bag 11, through filter 22 to the patient.

Second tubular branch 26 is connected to the other leg of Y-connection 24 and extends to the second lumen 29 of double lumen spike 18. It is typically intended that flow in second branch 26 always be in a direction away from the patient, back to bag 11 to carry only spent dialysis solution.

Slide clamp 30 controls the flow of dialysis solution in branches 20 and 26 to and from the patient.

Each of branches 20, 26 can optionally contain a drop forming member 31 to serve as a bubble trap, particularly in the inflow branch 20, and also to serve as flow rate indicator. Also, particularly in the case of outflow branch 26, drop forming member can provide means where drops are formed which fall through space to serve as a bacteria barrier, to prevent migration of bacteria upstream through the branch toward the patient. During the outflow phase, bag 11 is lowered and set 14 inverted, with drop forming tubes 33 being positioned as shown.

Branches 20, 26 may also each carry a one-way valve 35, positioned to permit flow only in the intended direction through each branch. One-way valve 35 in each case may be a duck-bill type valve or the like.

Referring now to FIG. 2, clamp 30 includes a slide member 32 and a housing 29 (FIG. 4) which, in the embodiment shown, has two component half sections 34, 36. Slide member 32 is a symmetrical unitary molded member, and includes elongated body portion 38 carrying two enlarged head sections 40 and 42 at its respective ends.

An elongated central slot 44 is provided, with two ribs or shoulders 46, 48 extending inwardly to define a narrow section of slot 44. Ribs 46, 48 do not extend the full length of slot 44, and thus branch tube-receiving openings 40 and 52 are defined at either end of the slot adjacent head sections 40 and 42 respectively. These openings freely receive tubing without constricting flow therein. Slot 44 between ribs 46 and 48 defines a branch tube-grasping section that will prevent flow through the grasped tube.

Housing half sections 34, 36 may be identical so that when assembled they will form the housing. Each section is generally U-shaped and has outwardly extending flanges 54, 56. One flange includes a pair of upwardly-extending sonically sealable protrusions 58, and the other flange includes a pair of protrusion-receiving apertures 62.

Legs 64, 65 of each housing section 34, 36 are spaced apart a distance slightly greater than the central width of slide member 32, and bight portion 66 includes a pair of tube-receiving apertures 67, 68. Apertures 67 and 68 are spaced apart a distance less than the distance between tube-receiving sections 50, 52 of slide member 32.

In order to assemble the clamp, slide member 52 is placed within the U-shaped section of one half section, such as 36, and the other half section 34 is then placed thereon in mating relationship. Then, protrusions 58 and protrusion-receiving openings 62 are sonic sealed together. Tubular branch 26 is threaded through housing openings 68 and section 50 of slide member 32. Branch 20 is threaded through openings 67 and section 52 of slide member 32, shifting slide member 32 to do it. Then set 14 is completely assembled.

Referring now to FIG. 3, the right-hand portion shows clamp 30 in cavity-drain position, whereby there is spent solution flowing through tubular branch 26 to bag 11, while branch 20 is sealed. The lefthand position of FIG. 3 shows the cavity-fill condition with branch 20 open and branch 26 in the closed position.

Referring to FIG. 4, the branches 20, 26 are shown grasped between flanges 46, 48 in a no-flow position.

FIGS. 4 through 6 show branches 20, 26 both pinched between flanges 46, 48 in a no-flow position.

Slide member 32 carries indicator marks 80, which are preferably of the width of slide housing 33 through which the slide member extends. Accordingly, when marks 80 are lined up with slide housing 20, as shown in FIG. 4, the user can know that both branches 20 and 26 are closed off. Alternatively, when shoulder 40 rests against housing 29, the user knows that branch 26 is open and branch 20 is closed. When shoulder 42 rests against housing 29, then the user knows that branch 20 is open and branch 26 is closed.

Figure 7:
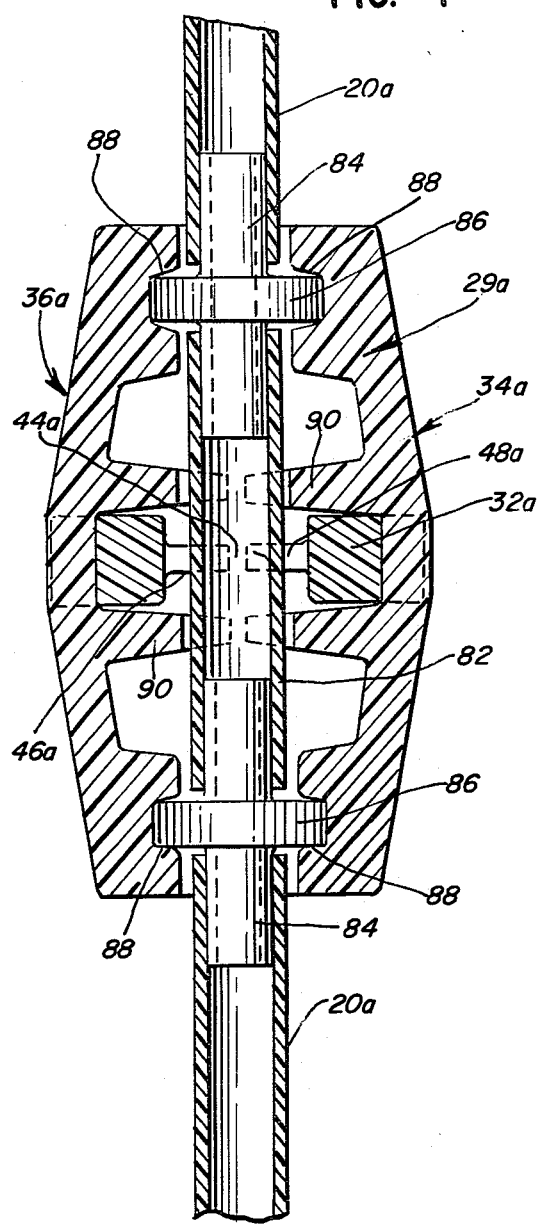
FIG. 7 is a longitudinal sectional view of a modified and preferred embodiment of this invention, also taken from a viewpoint similar to line 5—5 of FIG. 1, in which said clamp is carried on the tubular set in fixed position.

Referring to FIG. 7, a preferred embodiment of the clamp system of this invention is disclosed in which the clamp system is permanently retained in a single position on the tubing. It is similar to the FIG. 1 embodiment except as otherwise shown. As shown, tubular branch 20a carries an intermediate tubular section 82 which may be made out of a cross-linked elastomeric material such as silicone rubber or other cross-linked organic rubber. Tubular section 82 is connected to the respective lengths of tubular branch 20a by a conventional tubular connector member 84, each of which carry a flange 86 for retention of the connected housing halves 34a, 36a, which may be of analogous design to housing halves 34, 36, forming housing means 29a. Flanges 86 are positioned in corresponding recesses 88 at opposed ends of housing halves 34a, 36a, so that housing 29a is firmly retained on flanges 86. Connectors 84 may, in turn, be solvent sealed or otherwise adhered to the respective lengths of tubing 20a and 82. Tubing 20a may be made of a polyvinyl chloride formulation or other thermoplastic material.

Slide member 32a is provided, and may be of a structure similar to slide member 32 in the previous embodiment. Slide member 32a is shown to be at one of its terminal positions, in which tubing 82 passes through an enlarged end aperture of slot 44a. Flanges 46a, 48a are also provided to define slot 44a which is proportioned so that tube 82 may be closed in a similar manner to that of the previous embodiment. As a further advantage of this embodiment, since tubular branch section 82 is made of a thermoplastic material such as silicone rubber, there is little or no cold flow to worry about when it is forced into slot 44a, so the clamp shown in FIG. 7 operates in improved manner.

Inner prong members 90 are also provided in housing 29a to serve as guides for slide member 32a.

Figure 8:
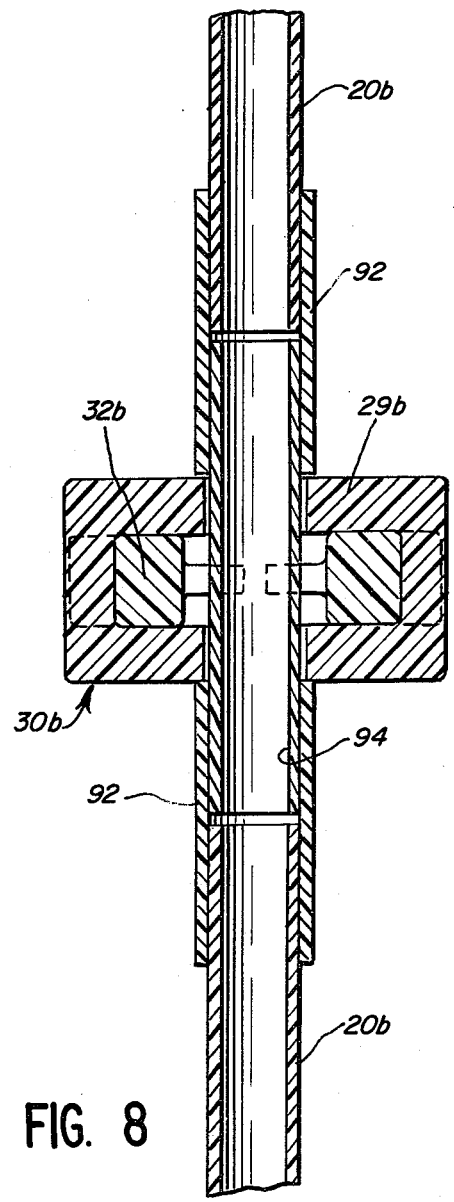
FIG. 8 is a longitudinal sectional view of another modified and also preferred embodiment, also taken from a viewpoint similar to line 5—5 of FIG. 1, and showing alternate means for retaining the clamp in fixed position relative to the set.

As a further embodiment, FIG. 8 is also similar in structure to the FIG. 1 embodiment, except as otherwise shown. Housing 29b of clamp 30b is carried in a fixed position on tubular branch 20b (and the other tubular branch) between a pair of retaining sleeve members 92, which may be suitably attached by gluing or solvent sealing to sections of tubular branch 20b. If desired, branch tubing portion 94 may be a separate piece adhering to sleeves 92 at opposed ends, being made of silicone or the like. Alternatively, branch tubing portion 94 may be an integral part of the entire tubular branch 20b, which may be made of a conventional thermoplastic material such as a polyvinyl chloride formulation or the like.

Slide member 32b is also shown as being of similar construction to slide members 32, 32a of the previous embodiments so that the tubular branches may be closed or opened in a manner dependent upon the position of slide member 32b.

In use, the set of this invention may be set up as shown in FIG. 1. Double lumen spike 18 penetrates into communication with solution container 11 through an access port. Slide member 32 is positioned to permit flow through tubular branch 20 so that peritoneal dialysis solution passes from container 11 through lumen 21 and branch 20, being filtered by filter 22 and permitted to flow through one-way valve 35 of branch 20 into the peritoneal cavity through catheter 12.

At the termination of flow, slide member 32 can be moved to its centered position so that both branches 20, 26 are closed as in FIG. 4.

When it is desired to remove the spent peritoneal dialysis solution, slide member 32 is moved to its opposite extreme position to open tubular branch 26, while branch 20 remains closed. In this instance the spent solution bypasses filter 22 and passes through lumen 29 of spike 18 back into container 11, so that lumen 21 of spike 18 connecting with branch 20 does not convey spent dialysis solution. Thus, when more fresh dialysis solution is to be added, the process can be repeated without any spent dialysis solution retained in lumen 21 being forced into contact with filter 22.

The above has been offered for illustrative purposes, and is not intended to limit the scope of the invention of this application, which is as defined in the claims below.

What is claimed is:

1. A flow control clamp for use in a peritoneal dialysis system in which a flow path having a pair of tubular branches is provided to connect a patient to a source of dialysis solution, with one branch for filling the peritoneal cavity with solution and one branch for draining the peritoneal cavity; said clamp selectively and alternatingly preventing flow in at least one branch and for preventing simultaneous flow in both branches, said clamp comprising an elongated slide member that includes a body portion having spaced ribs to define an open branch-receiving opening adjacent each end of said ribs and a narrowed branch-grasping and closing slot intermediate said openings between the ribs, and slide housing means constructed to retain said slide member in sliding relation therewith, said housing means having a pair of aperture means through which said branches pass, said aperture means being spaced apart a distance less than the distance between the open branch-receiving openings so as to prevent simultaneous alignment between the branches and both open branch-receiving openings, so that both branches cannot be open at the same time.

2. A clamp as in claim 1, wherein said housing comprises two half sections, each of said sections being a flanged U-shaped member interconnecting with the other half section to slidably enclose a section of the body portion of said slide clamp.

3. A clamp as in claim 1 wherein said slide member includes edge marking means to visually identify a predetermined position of said slide member relative to said housing.

4. A clamp as in claim 1 wherein said slide member includes an enlarged head section at each end of said body portion, each head section being adapted to engage said slide housing and limit the movement of said slide member.

5. The clamp of claim 1 which is carried on a tubular set for conveying peritoneal dialysis solution between a patient and a solution container, said clamp being retained in a fixed position adjacent the end of said set that connects with said solution container, said set having said tubular branches extending through said clamp for flow control therethrough.

6. The clamp of claim 5 in which said tubular branches each include a length of tubular, cross-linked elastomer as at least a part thereof, said lengths of tubular elastomer extending within said slide housing to be acted upon by said slide member, the remainder of said tubular set comprising tubing of a different, flexible thermoplastic formulation.

7. The clamp of claim 6 in which said lengths of tubular, cross-linked elastomer comprise silicone rubber.

8. The clamp of claim 7 in which the remainder of said tubular set comprises plasticized polyvinyl chloride.

9. The clamp of claim 5 which is carried in fixed position between a pair of retaining sleeve members which are attached to said tubular set.

10. The clamp of claim 5 in which said set has a double lumen spike at its end that connects with said solution container, said tubular branches each connecting with a separate lumen of said spike to define separate flow paths through said spike and branches.

11. The clamp of claim 1 in which each branch carries a one-way valve so that flow through each tubular branch is permitted only in a direction opposed to flow through the other branch.

12. The clamp of claim 1 in which one tubular branch carries a filter in flow communicating relation thereto.

13. The clamp of claim 1 in which each tubular branch defines a drip chamber to break liquid flow therethrough into discrete drops.

14. In a set for conveying peritoneal dialysis solution between a patient and a container for said solution: a flow control clamp, said set defining a flow path having a pair of tubular branches to connect the patient with said container, with one branch for conveying said solution to the patient and the other branch for withdrawing said solution from the patient back to the container, said clamp defining means selectively and alternatingly preventing flow in each branch while permitting flow in the other and for preventing simultaneous flow in both branches, the clamp also selectively providing simultaneous closure of both branches, said clamp means comprising an elongated slide member that includes a body portion having spaced ribs to define open branch-receiving openings adjacent each end of said ribs and a narrow branch-grasping closing slot intermediate said openings between the ribs, and slide housing means constructed to retain said slide member in sliding relation therewith, said housing means having a pair of aperture means through which said branches pass, said aperture means being spaced apart a distance less than the distance between the open branch-receiving openings so as to prevent simultaneous alignment between the branches and the open branch-receiving openings so that both branches cannot be opened at the same time.

15. The set of claim 14 in which said set has a double lumen spike at its end that connects with said solution container, said tubular branches each connecting with a separate lumen of said spike to define separate flow paths through said spike and branches.

16. The set of claim 15 in which said clamp is carried thereon in a fixed position adjacent said double lumen spike.

17. The set of claim 16 in which the branch permitting flow away from the said double lumen spike carries a filter in flow communicating relation thereto.

18. The set of claim 17 in which each branch carries a one-way valve so that flow through each branch is permitted only in a direction opposed to flow through the other branch.

19. The set of claim 17 in which each branch defines a drip chamber to break liquid flow therethrough into discrete drops.

20. The set of claim 17 in which said slide member includes an enlarged head section at each end of said body portion, each head section being adapted to be engagable with said sliding housing to limit movement of said slide member in one direction.

21. The set of claim 20 in which said slide member includes edge marking means to visually identify a predetermined position of said slide member relative to said housing.

22. The set of claim 20 in which said tubular branches each include a length of tubular, cross-linked elastomer as at least a part thereof, said length of tubular elastomer extending within said slide housing to be acted upon by said slide member, the remainder of said tubular set comprising tubing of a different, flexible, thermoplastic formulation.

23. The set of claim 22 in which said tubular cross-linked elastomer is silicone rubber, and said different, flexible, thermoplastic formulation is a polyvinyl chloride formulation.

24. The set of claim 20 in which said clamp means is carried in fixed position adjacent said double lumen spike between a pair of retaining sleeve members which are attached to said tubular set.

* * * * *